United States Patent [19]

Willemot et al.

[11] Patent Number: 5,219,755
[45] Date of Patent: Jun. 15, 1993

[54] PROCESS FOR THE CULTURE OF ANAEROBICS GERMS

[75] Inventors: Jean-Marie Willemot, Sceaux; Robert Briend, Les Clayes Sous Bois, both of France

[73] Assignee: L'Air Liquide, Societe Anonyme pour l'Etude et l'Exploitation des Procedes Georges Claude, Paris, France

[21] Appl. No.: 703,787

[22] Filed: May 21, 1991

[30] Foreign Application Priority Data

Jun. 7, 1990 [FR] France .................. 90 07077

[51] Int. Cl.$^5$ .................. C12N 1/00
[52] U.S. Cl. .................. 435/243; 435/801; 435/296; 435/313
[58] Field of Search .................. 435/3, 29, 30, 34, 32, 435/39, 40, 243, 287, 289, 296, 297, 298, 299, 300, 310, 311, 313, 351, 801, 809, 260

[56] References Cited

U.S. PATENT DOCUMENTS

| | | | |
|---|---|---|---|
| 3,483,089 | 12/1969 | Brewer | 435/801 |
| 3,562,114 | 2/1971 | Steidl et al. | 435/297 |
| 3,775,256 | 11/1973 | Risinger | 435/801 |
| 4,111,753 | 9/1978 | Folsom et al. | 435/801 |
| 4,162,196 | 7/1979 | Folsom et al. | 435/801 |
| 4,458,019 | 7/1984 | Chrisope | 435/801 |
| 4,473,552 | 9/1984 | Jost | 435/2 |
| 4,686,188 | 8/1987 | Whitley | 435/801 |

FOREIGN PATENT DOCUMENTS

| | | |
|---|---|---|
| 0168915 | 1/1986 | European Pat. Off. . |
| 0262037 | 11/1988 | German Democratic Rep. . |
| 0591359 | 2/1978 | U.S.S.R. . |
| 0800192 | 1/1981 | U.S.S.R. .................. 435/801 |
| 0810803 | 3/1981 | U.S.S.R. .................. 435/313 |
| 2174714 | 11/1986 | United Kingdom . |

*Primary Examiner*—Michael G. Wityshyn
*Assistant Examiner*—William H. Beisner
*Attorney, Agent, or Firm*—Oliff & Berridge

[57] ABSTRACT

The process comprises circulation in a vessel containing the germs during a time $T_1$ a ternary gas mixture comprising about 5% carbon dioxide, between 3.5 and 5% hydrogen; the balance consisting of nitrogen, followed by sealingly closing the vessel containing this gas mixture, advantageously under a slight overpressure, these operations are carried out automatically by means of an assembly comprising a gas feeding line and a gas outlet line each provided with an electro-valve and being electronically controlled.

10 Claims, 1 Drawing Sheet

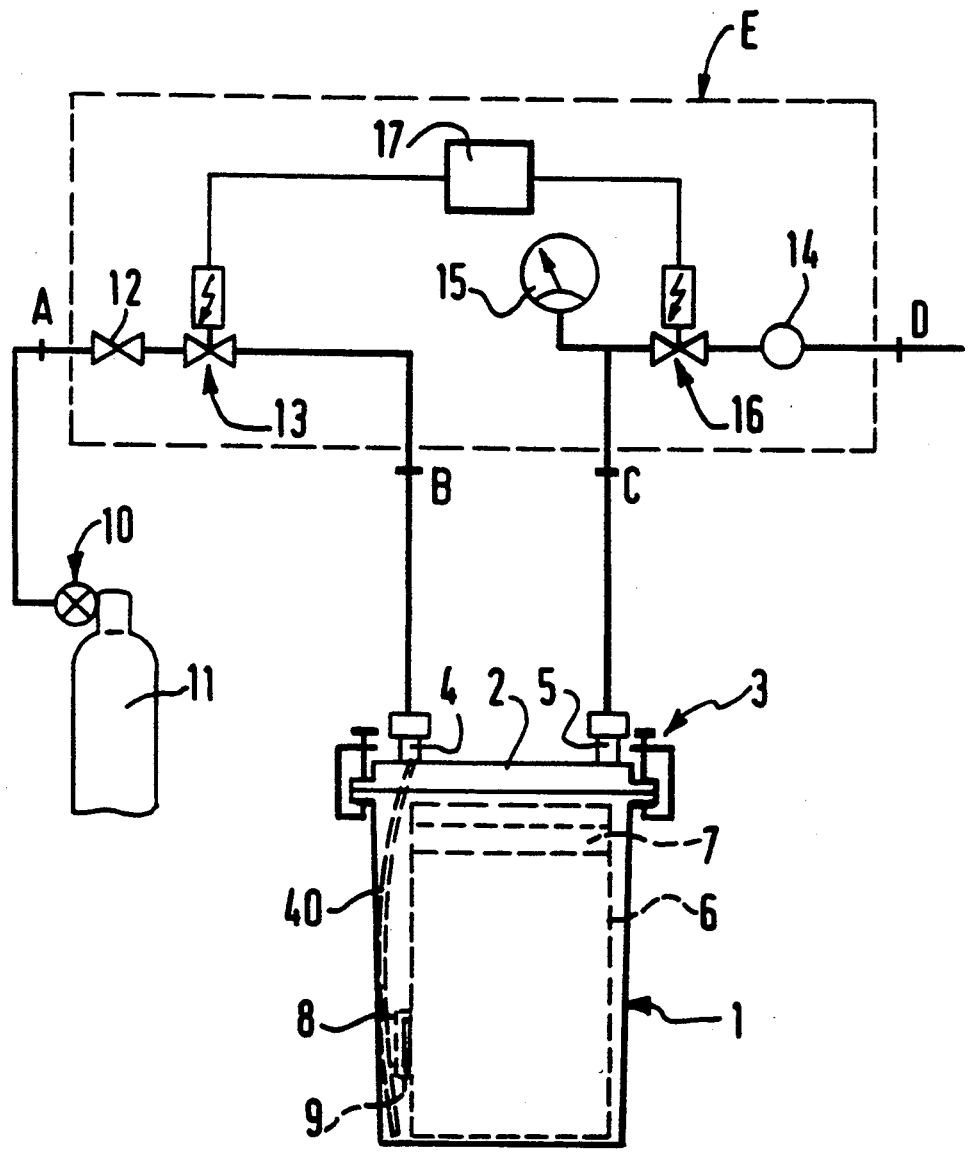

PROCESS FOR THE CULTURE OF ANAEROBICS GERMS

BACKGROUND OF THE INVENTION a. Field of the Invention

The present invention concerns a process and an apparatus for culturing strict anaerobic germs in a vessel, including the preliminary step, before incubating the germs, of providing in the vessel containing the germs and a palladium catalyst, a gaseous atmosphere which is free of oxygen and which comprises carbon dioxide and hydrogen.

b. Description of Prior Art

The known processes for obtaining conditions of anaerobiosis in such vessels utilise gas generating bags in the form of effervescent tablets releasing, in the vessel, carbon dioxide and hydrogen in excess under initial conditions and providing in the recipient a non-controlled gas atmosphere whose composition varies substantially in time. On the other hand, the systematic utilisation of bags before each phase of incubation contributes to the relatively high cost of this technique.

A so called withdrawal and filling technique has also been proposed according to which the vessel undergoes a certain number (at least 6 and possibly 12) of consecutive cycles of partial exhaustion of the vessel followed by the introduction of a gas consisting of nitrogen or a mixture containing carbon dioxide and hydrogen. This technique has also been found to be costly inasmuch as in addition to the compulsory use of a vacuum pump, the consecutive cycles represent a substantial gas consumption and take a certain time.

SUMMARY OF THE INVENTION

It is an object of the present invention to propose a new process which overcomes the disadvantages of the known processes, which is of rapid execution, of substantially reduced cost and warrants controlled conditions of anaerobiosis which are favourable to bacterial cultures, and for this reason are interesting more particularly for independent laboratories of medical analysis, and laboratories of microbiological control, such as in the agro-food and cosmetic industries.

To achieve this object, according to a characteristic of the invention, the process comprises the steps of circulating in the vessel, during a time $T_1$, a gas mixture containing about 5% carbon dioxide, between 3 and 10%-typically between 3.5 and 5%-hydrogen, the balance consisting of nitrogen, followed by sealing the vessel containing said gas mixture.

More specifically, for a vessel having a volume of about 3.5 liters, the circulation flow of the gas mixture is about 1 liter per minute, time $T_1$ being higher than or equal to 13 minutes, typically between 14 and 17 minutes.

It is also an object of the present invention to provide an apparatus for carrying out this process, which is of simple design and low cost and enabling a thorough automation of the step of providing a controlled gas atmosphere in the vessel.

To achieve this, according to another characteristic of the invention, the apparatus, of the type comprising: a vessel which is sealable by means of a cover provided with a gas inlet connector with check valve and an outlet gas connector with check valve, provided with storage arrangement for germ containers and a housing for a bag of catalyst, and a bottle of a gas mixture comprising carbon dioxide and hydrogen, which can be connected to the inlet gas connector through a distribution pressure reducer valve, additionally comprises a distribution and control device containing a gas inlet line which can be connected between the pressure reducer valve and the gas inlet connector of the vessel and which is provided with a first electro-valve, and control means to automatically activate the first electro-valve.

BRIEF DESCRIPTION OF DRAWINGS

Other characteristics and advantages of the present invention will appear from the description which follows of an embodiment, given by way of illustration but without limitation, with reference to the annexed drawing in which:

The single FIGURE is a schematic representation of an apparatus according to the invention.

DESCRIPTION OF PREFERRED EMBODIMENTS

The drawing shows a vessel for anaerobiosis 1, normally called "jar" which is sealable by means of a cover 2 that can be locked by means of at least one clip 3, the cover being provided with an inlet gas connector 4 provided with a check valve allowing passage only in a direction towards the inside of the vessel, and an outlet gas connector 5 provided with a check valve allowing passage only in a direction outside the vessel. The latter also comprises an element or a basket 6 for housing a germ recipient, typically Petri boxes 7 which can be piled over one another, or test tubes. According to the invention the basket 6 is provided, in the vicinity of its base, with a housing 8 for a bag 9 of a palladium catalyst enabling, at low temperature, to combine hydrogen and oxygen and therefore converting into water the traces of residual oxygen in the sealed vessel. The gas inlet connector 4 is extended towards the interior by means of a flexible duct 40 extending to the vicinity of the bottom of the vessel 1.

The apparatus according to the invention comprises a distribution and control unit including a gas inlet line A-B which can be connected between a pressure reducer valve 10 of a bottle of gas mixture 11 and the connector 4. Line A-B comprises, from the upstream end to the downstream end, a flow regulator valve 12, and a first electro-valve 13. The distribution and control unit also includes a gas return line C-D which can be connected to the connector 5 and opens at D into the atmosphere or can be connected to a recovery tank. Line C-D comprises, from the upstream end to the downstream end, a manometer 15, a second electro-valve 16 and a flow meter 14. The unit is completed by means of an electronic control box 17 connected to the electro-valves 13 and 16 and, possibly, to a manometer 15 of the manostat type, and including a program selectively activating the electro-valves 13 and 16, the and the second electro-valve 16 being typically of the type normally open. The distribution and control unit is advantageously integrated into a box E comprising fast connections at the level of the interfaces A to C.

According to an aspect of the invention, bottle 11 contains a gas mixture containing about 5% carbon dioxide, between 3.5 and 5%, typically 4.5% hydrogen, the balance consisting of nitrogen.

The process according to the invention operates as follows: vessel 1, containing the catalyst 9 and a series of germ containers 7, is sealed by means of cover 2 through clips 3. Lines A-B and D-C are then connected, for example by means of joints of the type for rapid connection, to the connectors 4 and 5. Valve 10 of bottle 11 is opened and, valve 12 and the electro-valves 13 and 16 are opened, the gas mixture present in the bottle 11 is circulated in the vessel 1 for a time $T_1$ which is sufficient to provide a suitable scavenging of the inner volume of the vessel 1 and thus remove nearly all the air which was initially present. After time $T_1$, control box 17 activates the closing of the electro-valve 16 for a time $T_2$ which produces a progressive pressurization of the vessel 1, after which box 17 activates the closing of the electro-valve 13. An alarm is then triggered, signaling the end of the conditioning. Vessel 1 is thus insulated from the source of gas under pressure 11 and the atmosphere, lines A-B and C-D are disconnected from the connectors 4 and 5 and the vessel 1, thus conditioned, can be placed into an oven, typically for a period of 24 hours.

For a conventional vessel 1, of an internal capacity of 3.5 liters, the valve 12 is adjusted so as to allow a flow of circulating gas of about 1 liter per minute for a time $T_1$ not lower than 13 minutes, typically between 14 and 17 minutes, preferably during 16 minutes. It will be noted here that, to insure good conditions of anaerobiosis, the time and circulation flow should be very precisely matched.

The pressure reducer 10 produces a gas mixture under a low pressure typically of $2 \times 10^5$ Pa (2 bars) absolute, to give, in view of the losses of charge of line A-B, at the level of the connector 4 a slight over-pressure, typically of the order of $6 \times 10^4$ Pa (0.6 bar). At the end of time $T_1$, the electro-valve 16 is closed for a time $T_2$, of the order of 50 to 60 seconds, which is sufficient to produce in vessel 1 a safety over-pressure between 150 and 250 hPa, typically of the order of 200 hPa, against dangers of loss at the level of the cover 2.

Although the invention has been described with respect to an embodiment, it is not limited thereby, but on the contrary, it is susceptible to modifications and variants which will appear to one skilled in the art, for example in connection with the shapes and capacities of the vessels 1.

We claim:

1. A process of storing anaerobes under a controlled anaerobic atmosphere, comprising the steps of:

providing a vessel sealable by a cover having first and second connection means for connection to first and second gas circuits, respectively;

placing within the vessel a catalyst and anaerobes to be stored;

closing the vessel by the cover;

providing a source of a mixture of gases including about 5% $CO_2$, between 3-10% $H_2$, balance nitrogen;

connecting the source to a first gas circuit;

connecting the first and second connection means to the first gas circuit and to a second exhaust gas circuit, respectively;

circulating the gas mixture from the first gas circuit to the second gas circuit via the vessel for a predetermined period of time;

temporarily closing the second gas circuit to create within the vessel an overpressure of the gas mixture;

disconnecting the first and second connection means from the first and second gas circuits;

sealing the vessel with respect to the ambient atmosphere.

2. The process of claim 1, wherein the gas mixture is circulated at a substantially constant flow during the predetermined period.

3. The process of claim 1, wherein the first and second connection means each include a non-return valve.

4. The process of claim 1, wherein the hydrogen content of the gas mixture is between 3.5 and 5%.

5. The process of claim 2, wherein the circulation rate of the gas mixture during the predetermined period is about 1 liter per minute in an about 3.5 liter vessel.

6. The process of claim 2, wherein the predetermined period does not exceed 17 minutes.

7. The process of claim 3, wherein the vessel is a transportable jar.

8. The process of claim 7, further comprising the step of placing the sealed vessel in an incubator.

9. The process of claim 7, wherein the jar has a bottom, comprising the step of introducing into the jar the gas mixture from the first gas circuit adjacent the bottom of the jar.

10. The process of claim 9, comprising the steps of placing the anaerobes in a supporting basket in the vessel, the basket carrying the catalyst, and of placing the basket within the jar.

* * * * *